(12) United States Patent
Ghajar (10) Patent No.: US 7,819,818 B2
(45) Date of Patent: Oct. 26, 2010

(54) COGNITION AND MOTOR TIMING DIAGNOSIS USING SMOOTH EYE PURSUIT ANALYSIS

(76) Inventor: Jamshid Ghajar, 110 E. 71st St., #3, New York, NY (US) 10021

( * ) Notice: Subject to any disclaimer, the term of this patent is extended or adjusted under 35 U.S.C. 154(b) by 1141 days.

(21) Appl. No.: 11/245,305

(22) Filed: Oct. 5, 2005

(65) Prior Publication Data

US 2006/0270945 A1 Nov. 30, 2006

Related U.S. Application Data

(63) Continuation-in-part of application No. 10/834,356, filed on Apr. 27, 2004, now Pat. No. 7,384,399.

(51) Int. Cl.
| | |
|---|---|
| A61B 13/00 | (2006.01) |
| A61B 5/103 | (2006.01) |
| A61B 5/117 | (2006.01) |
| G08B 21/00 | (2006.01) |
| G08B 23/00 | (2006.01) |

(52) U.S. Cl. .................. 600/558; 600/587; 600/595; 340/540; 340/573.1

(58) Field of Classification Search ........... 600/300, 600/301, 544, 545, 546, 547, 558, 587, 595, 600/559; 351/200, 201, 203, 205, 206; 128/920, 128/922, 923, 924, 925; 382/100, 110, 115, 382/117; 340/540, 573.1, 576
See application file for complete search history.

(56) References Cited

U.S. PATENT DOCUMENTS

| | | | |
|---|---|---|---|
| 4,332,566 A | 6/1982 | Mazeski et al. ............ 434/178 |
| 4,407,299 A * | 10/1983 | Culver .................... 600/544 |
| 4,838,681 A | 6/1989 | Pavlidis .................... 351/210 |
| 4,889,422 A | 12/1989 | Pavlidis .................... 351/210 |

(Continued)

FOREIGN PATENT DOCUMENTS

EP 1726260 A2 11/2006

OTHER PUBLICATIONS

International Search Report for International Application No. PCT/US2006/032773, mailed Jan. 22, 2007.

(Continued)

*Primary Examiner*—Max Hindenburg
*Assistant Examiner*—Jeffrey G Hoekstra
(74) *Attorney, Agent, or Firm*—Morgan, Lewis & Bockius LLP (57) ABSTRACT

A system for testing a subject for cognitive impairment includes a display, one or more video cameras and a computer. The display presents to the subject multiple stimuli, including a predictable, smoothly moving object, repeatedly moving over a same path. The video cameras sense eye movements of the subject, while the subject visually follows the object on the display. The computer analyzes the subject's eye movements to determine, for example, accuracy and variability of the subject's visual pursuit of the display of the smoothly moving object, and determines, based on the analysis, if the subject has a cognitive impairment. The analysis may provide one or more metrics, such as a metric of attention, a metric of fatigability and a metric of distractibility. The system may also be configured to provide feedback signals to the user, in which case the system also functions as cognition timing and motor training system.

18 Claims, 7 Drawing Sheets

U.S. PATENT DOCUMENTS

| | | | | |
|---|---|---|---|---|
| 5,137,027 | A * | 8/1992 | Rosenfeld | 600/544 |
| 5,331,969 | A * | 7/1994 | Silberstein | 600/544 |
| 5,491,492 | A | 2/1996 | Knapp et al. | 345/8 |
| 5,529,498 | A | 6/1996 | Cassily et al. | 434/258 |
| 5,662,117 | A * | 9/1997 | Bittman | 600/545 |
| 5,743,744 | A * | 4/1998 | Cassily et al. | 434/258 |
| 5,867,587 | A * | 2/1999 | Aboutalib et al. | 382/117 |
| 6,090,051 | A | 7/2000 | Marshall | 600/558 |
| 6,102,870 | A | 8/2000 | Edwards | 600/558 |
| 6,162,186 | A | 12/2000 | Scinto et al. | 600/558 |
| 6,603,491 | B2 * | 8/2003 | Lemelson et al. | 715/784 |
| 2002/0099305 | A1 | 7/2002 | Fukushima et al. | 600/558 |
| 2005/0177065 | A1 | 8/2005 | Ghajar | 600/558 |

OTHER PUBLICATIONS

Gredeback, G., et al., "The Development of Two-Dimensional Tracking: A Longitudinal Study of Circular Pursuit," Experimental Brain Research, vol. 163, No. 2, May 2005, pp. 204-213.

Kathmann, N., et al., "Deficits in Gain of Smooth Pursuit Eye Movements in Schizophrenia and Affective Disorder Patients and Their Unaffected Relatives," The American Journal of Psychiatry, vol 160, No. 4, Apr. 2003, pp. 696-702.

Ball et al., "The Role of Higher-Order Motor Areas in Voluntary Movement as Revealed by High-Resolution EEG and fMRI", NeuroImage, (1999) 10:682-694.

Barnes, et al., "Anticipatory Control of Hand and Eye Movements in Humans During Oculo-Manual Tracking", J. of Physiology, (2002) 539.1:317-330.

Chan et al., "Are There Sub-types of Attentional Deficits in Patients with Persisting Post-Concussive Symptoms? A Cluster Analytical Study", Brain Injury (2003) 17(2):131-148.

Gibbon et al., "Toward a Neurobiology of Temporal Cognition: Advances and Challenges", Current Opinion in Neurobiology, (1997) 7:170-184.

Green et al., "Deficits in Facial Emotion Perception in Adults with Recent Traumatic Brain Injury", Neuropsychologia, (2004) 42:133-141.

Hulsmann et al., "From Will to Action: Sequential Cerebellar Contributions to Voluntary Movement", NeuroImage, (2003) 20:1485-1492.

Lewine et al., "Neuromagnetic Assessment of Pathophysiologic Brain Activity Induced by Minor Head Trauma", AJNR Am. J. Neuroradiol., (May 1999) 20:857-866.

Lutz et al., "Guiding the Study of Brain Dynamics by Using First-Person Data: Synchrony Patterns Correlate with Ongoing Conscious States During a Simple Visual Task", PNAS, (Feb. 5, 2002) 99(3):1586-1591.

Madelain et al, "Effects of Learning on Smooth Pursuit During Transient Disappearance of a Visual Target", J. Neurophysiol., (2003) 90:972-982.

Mangels et al., "Effects of Divided Attention on Episodic Memory in Chronic Traumatic Brain Injury: A Function of Severity and Strategy", Neuropsychologia, (2002) 40:2369-2385.

Mehta et al., "Forward Models in Visuomotor Control", J. Neurophysiol., (2002) 88:942-953.

Pedersen et al., "Origin of Human Motor Readiness Field Linked to Left Middle Frontal Gyrus by MEG and PET", NeuroImage, (1998) 8:214-220.

Perbal et al., "Relationships Between Time Estimation, Memory, Attention, and Processing Speed in Patients with Severe Traumatic Brain Injury", Neuropsychologia, (2003) 41:1599-1610.

Smith et al., "A Right Hemispheric Frontocerebellar Network for Time Discrimination of Several hundreds of Milliseconds", NeuroImage, (2003) 20:344-350.

Strauss et al., "Intraindividual Variability in Cognitive Performance in Three Groups of Older Adults: Cross-domain Links to Physical Status and Self-Perceived Affect and Beliefs", J. of the International Neuropsychol. Soc., (2002) 8:893-906.

* cited by examiner

COGNITION AND MOTOR TIMING DIAGNOSIS USING SMOOTH EYE PURSUIT ANALYSIS

This application is a continuation-in-part application (CIP) of U.S. patent application Ser. No. 10/834,356, filed Apr. 27, 2004, now U.S. Pat. No. 7,384,399, entitled "Cognition and Motor Timing Diagnosis and Training System and Method," which is hereby incorporated by reference.

TECHNICAL FIELD

The disclosed embodiments relate generally to systems and methods of testing a person's ability to anticipate stimuli, as well as remedial systems and methods for improving a person's ability to accurately anticipate the timing of predictable events or stimuli.

BACKGROUND

Anticipation or expectation of a sensory event that must be paired with an action is essentially a form of attention that is crucial for an organism's interaction with the external world. The accurate pairing of sensation and action, assuming these functions are intact, is dependent on timing and is called sensory-motor timing, one aspect of which is anticipatory timing. Anticipatory timing is essential to successful everyday living, not only for actions but also for thinking. Thinking or cognition can be viewed as an abstract motor function and therefore also needs accurate sensory-cognitive timing. Sensory-motor timing is the timing related to the sensory and motor coordination of an organism when interacting with the external world. Anticipatory timing is usually a component of sensory-motor timing and is literally the ability to predict sensory information before the initiating stimulus.

Anticipatory timing is essential for reducing reaction times and improving both movement and thought performance. Anticipatory timing only applies to predictable sensory-motor or sensory-thought timed coupling. The sensory modality (i.e., visual, auditory etc.), the location, and the time interval between stimuli, must all be predictable (i.e., constant, or consistent with a predictable pattern) to enable anticipatory movement or thought.

Without reasonably accurate anticipatory timing, a person cannot catch a ball, know when to step out of the way of a moving object (e.g., negotiate a swinging door), get on an escalator, comprehend speech, concentrate on mental tasks or handle any of a large number of everyday tasks and challenges. This capacity for anticipatory timing can become impaired with aging, alcohol, drugs, hypoxia, infection, clinical neurological conditions including but not limited to Attention Deficit Hyperactivity Disorder (ADHD), schizophrenia, autism and brain trauma (head injury or concussion). For example, brain trauma may significantly impact a person's cognition timing, one aspect of which is anticipatory timing. Sometimes, a person may appear to physically recover quickly from head or brain trauma, but have significant problems with concentration, memory, headaches, irritability and other symptoms as a result of impaired anticipatory timing. In addition, impaired anticipatory timing may cause the person to suffer further injuries by not having the timing capabilities to avoid accidents.

SUMMARY

A system for testing a subject for cognitive impairment includes a display, one or more video cameras and a computer. The display presents to the subject multiple stimuli, including a predictable, smoothly moving object, repeatedly moving over a same path. The video cameras sense eye movements of the subject, while the subject visually follows the object on the display. The computer analyzes the subject's eye movements to determine, for example, accuracy and variability of the subject's visual pursuit of the display of the smoothly moving object, and determines, based on the analysis, if the subject has a cognitive impairment. The cognitive impairment may be an anticipatory timing impairment. The analysis may provide one or more metrics, such as a metric of attention, a metric of fatigability and a metric of distractibility. The system may also be configured to provide feedback signals to the user, in which case the system also functions as a cognition timing and motor training system.

BRIEF DESCRIPTION OF THE DRAWINGS

Like reference numerals refer to corresponding parts throughout the several views of the drawings.

DESCRIPTION OF EMBODIMENTS

Since it is extremely difficult to measure thinking performance without a movement and since a similar neural network is used for anticipatory timing, cognition and motor timing are linked. Therefore diagnosis and therapy can be performed for anticipatory timing difficulties in the motor and cognitive domains using motor reaction times and accuracy. In particular, both the reaction time and accuracy of a subject's movements can be measured. As discussed below, these measurements can be used for both diagnosis and therapy.

Anticipatory cognition and movement timing are controlled by essentially the same brain circuits. Variability or a deficit in anticipatory timing produces imprecise movements and disrupted thinking, such as difficulty in concentration, memory recall, and carrying out both basic and complex cognitive tasks. Such variability and/or deficits leads to longer periods of time to successfully complete tasks and also leads to more inaccuracy in the performance of such tasks. Some embodiments of the present invention measure such variability or deficits to determine whether a person suffers impaired anticipatory timing. Some embodiments of the present invention use a sequence of stimuli in combination with a feedback mechanism to train a person to improve anticipatory timing.

Sequenced stimuli presented to a subject may include sequences of both predictable and non-predictable (e.g., random or pseudo-random) stimuli. In one embodiment, the non-predictable stimuli are presented to a subject before the predictable stimuli. The stimuli can use any sensory modality. In some embodiments, the stimuli are visual stimuli. In other embodiments, the stimuli are auditory. While other forms of stimuli can be used, the embodiments described here use visual stimuli. The subject's responses may be visual, manual or even spoken. In some embodiments the subject's responses are measured by tracking eye movement. In other embodiments, the subject's responses are measured by a mechanical, piezoelectric or other sensors activated by physical movement of the subject, such as pressing a button. In yet other embodiments, a frontal brain electroencephalographic (EEG) signal (e.g., the "contingent negative variation" signal) is measured during the period before a subject's response. The amplitude of the EEG signal is proportional to the degree of anticipation and will be disrupted when there are anticipatory timing deficits.

Figure 1:
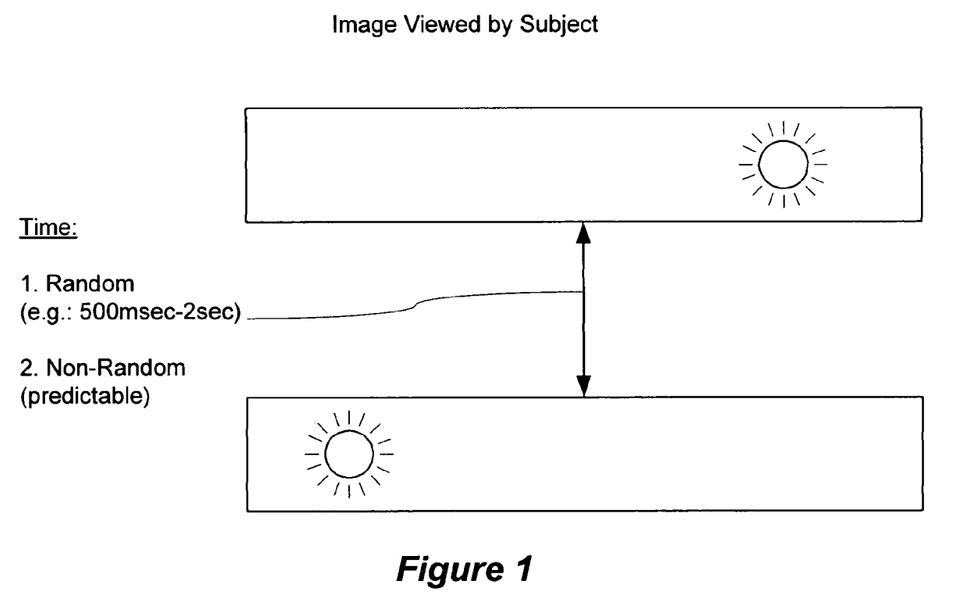
FIG. 1 illustrates a sequence of stimuli presented to a person, in this case two circles that alternately go on and off in a predictable or random fashion.

FIG. 1 depicts a sequence of visual stimuli. The subject's task is to follow the illuminated circle, which will alternate between two locations at a random (non-predictable) or non-random (predictable) rate. In one embodiment the random rate is between 500 msec to 2 sec. The subject may indicate that the circle is illuminated at a particular location by activating a sensor, or by moving his/her eyes to focus on the illuminated circle on the screen. In another example, the subject may indicate that the circle is illuminated at a particular location by controlling the position of an image of an object on a screen using a joystick or other user input mechanism, and may be asked to move the object so as to "catch" a moving object, or to avoid being hit by another object, or to move the object so as to match the movement of a computer generated image, or other similar exercise.

In yet another example, multiple objects, such as images of circles, are displayed in a row or other pattern. The objects are flashed on and off in a predictable or random fashion. Eye movement reaction times are measured by a digital video infrared camera focused on the subject's pupil, operating at a picture update rate of at least 200 hertz. The resulting digital video signal is analyzed by a computer to determine the screen position(s) where the subject was focusing, and the timing of when the subject focused at the appropriate screen position. If feedback is provided, the feedback may be provided by giving the subject a tone, using either open air audio speakers or headphones, or by having the color of the display change when the subject's anticipatory timing is within a normal or desired distribution.

In some embodiments, the stimuli presented to the subject include one or more sequences of non-predictable stimuli. The non-predictable stimuli can be random or pseudorandom sequences. The sequences of non-predictable stimuli cannot be learned and there is therefore no anticipatory timing by the subject. Measurements of the timing of the subject's responses to the sequences of non-predictable stimuli can be used as an internal control. These measurements are measurements of the subject's reactive timing. Subtracting the subject's reactive timing from the subject's anticipatory timing produces the subject's absolute anticipatory timing. By taking numerous timing measurements of the subject's responses to sequences of non-predictable stimuli, a distribution of such timing measurements is generated. The distribution can be graphed or displayed, compared with normative data for a population of other subjects, and the like.

Next, the stimuli presented to the subject also include multiple sequences of predictable stimuli. An initial phase in which the sequences of predictable stimuli are presented is called the learning phase. During the learning phase there is typically a progressive shift toward earlier correct reactions, and thus anticipatory timing. It is noted that in some embodiments, incorrect reactions by the subject are eliminated or not used for purposes of evaluating anticipatory timing. After the learning phase, there should be an anticipatory reaction phase during which the subject's response times are relatively static or fixed. The subject response times during the anticipatory reaction phase will generally be earlier than the initial responses during the learning phase. These response times, herein called anticipatory timing, will also be shorter than the subject's reactive timing to non-predictable stimuli.

By testing the subject with numerous sequences of predictable stimuli and taking measurements of the subject's anticipatory timing, a distribution of such timing is generated. The distribution can be graphed or displayed, compared with normative timing data for a population of other subjects, and the like.

Figure 2A:
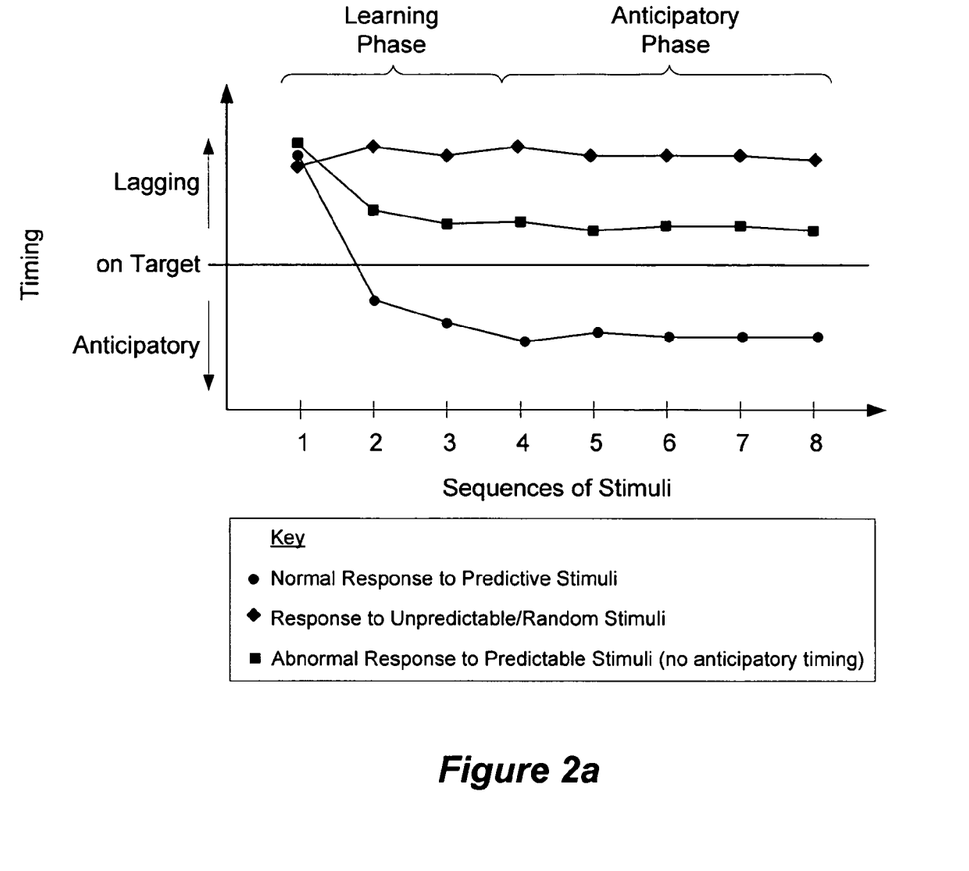
FIG. 2a illustrates a subject's response timing to sequences of stimuli, both for predictable and random stimuli.

FIG. 2a is a prophetic example of a graph of typical response timings to sequences of stimuli, both for predictable and random stimuli. For purposes of this discussion the terms "normal subject" and "abnormal subject" are defined as follows. Normal subjects are typically healthy individuals whose sensory-motor or anticipatory timing falls within a normal performance range. Abnormal subjects are individuals suffering from impaired brain function with respect to sensory-motor or anticipatory timing.

As represented in FIG. 2a, even normal, health subjects responding to random stimuli (♦) cannot anticipate the exact timing of the stimuli, and thus they lag behind being "on target." In other words, even after a learning phase where the user is subjected to a number of sequences of stimuli, the normal user cannot anticipate a subsequent sequence of random stimuli.

Normal subjects responding to predictable stimuli (●), such as a repeating sequence of visual stimuli, after a learning phase start to anticipate the stimuli before they are presented to the subjects. During a learning phase the normal subjects learn the sequence of stimuli and are then able to anticipate the stimuli during an anticipatory phase. Abnormal subjects (■), however, only slightly improve their response timing after the learning phase and still cannot anticipate the stimuli during the anticipatory phase. In other words, abnormal subjects may improve their response timing during training, but cannot anticipate subsequent stimuli as well as a typical normal subject.

Figure 2B:
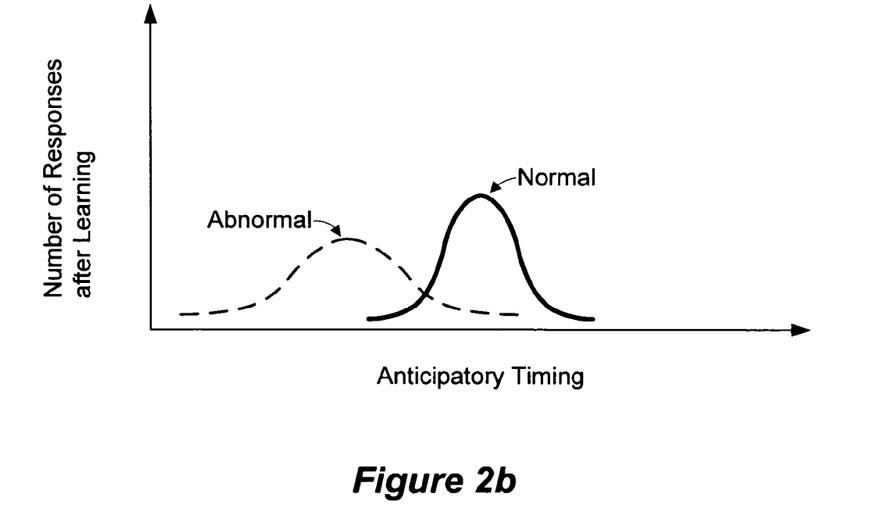
FIG. 2b shows normal and abnormal distributions of anticipatory timing.

FIG. 2b is a prophetic example of the distribution of anticipatory response timing of an abnormal subject and the average anticipatory response timing of a control group of normal subjects. An abnormal distribution of anticipatory response timing is typically slower, on average than the normal distribution. The abnormal subject also typically has more inaccurate responses. Even more significantly, the width of an abnormal anticipatory timing distribution is typically significantly wider than the width of a normal anticipatory timing distribution. In some embodiments, the width of a distribution may be defined as the full width of the distribution at half maximum (sometimes called FWHM). In some embodiments, the width of a subject's anticipatory timing distribution is defined as the variance of the response distribution, the standard deviation of the response distribution, the average deviation of the response distribution, the coefficient of variation of the response distribution, or any other appropriate measurement of the width of the response distribution.

In some embodiments, as described above, the subject's reactive timing is subtracted from the subject's anticipatory timing to produce the subject's absolute anticipatory timing.

In some embodiments, this is accomplished by subtracting an average reactive timing value from the anticipatory timing values.

The subject's absolute anticipatory timing distribution can be compared with the absolute anticipatory timing distribution of a control group of subjects. Both the average timing and the width of the timing distribution, as well as their comparison with the same parameters for a control group are indicative of whether the subject is suffering from a cognitive timing impairment.

Figure 3:
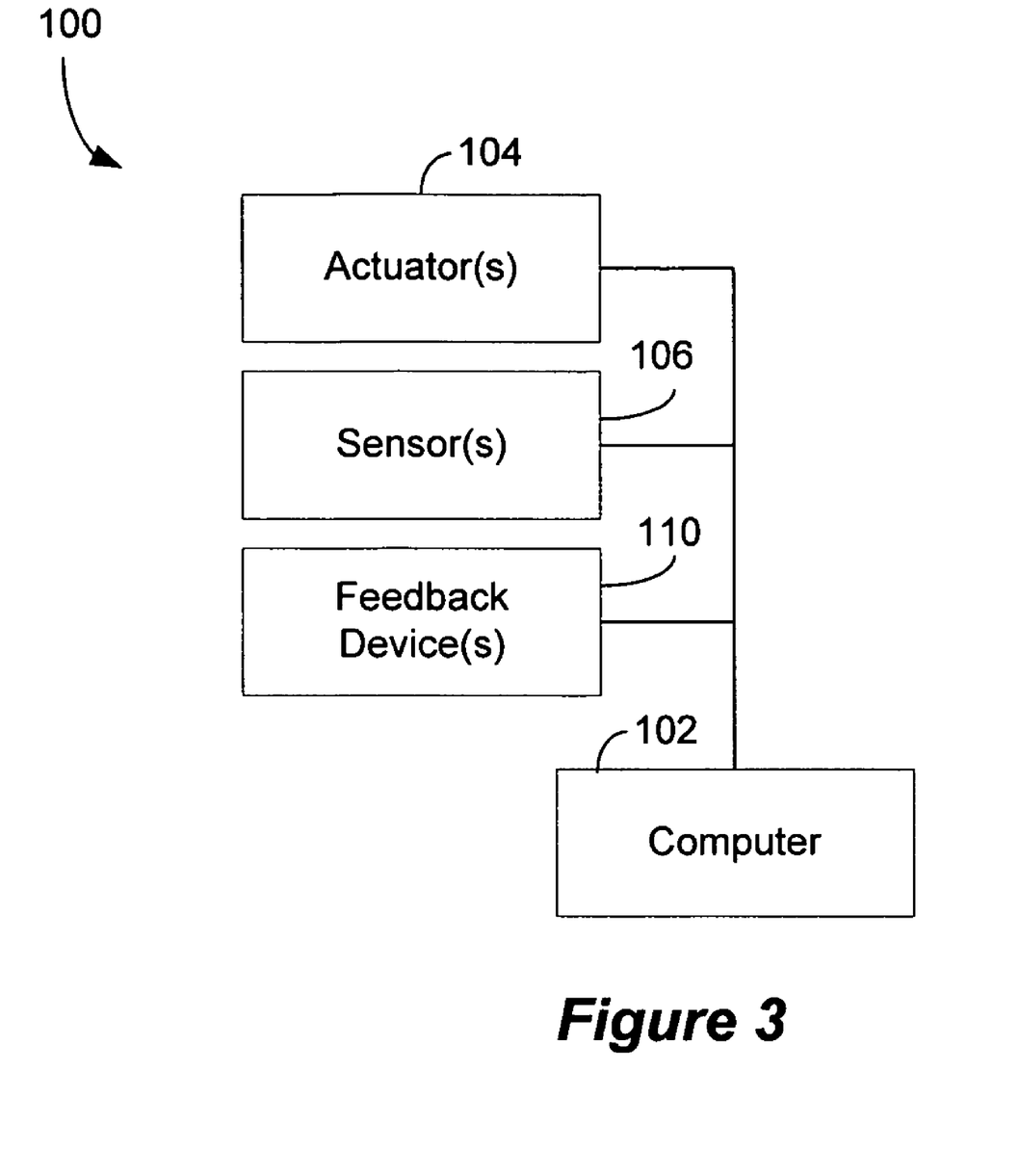
FIG. 3 is a conceptual block diagram of a cognition timing diagnosis and training system.

FIG. 3 is a conceptual block diagram of a cognition timing diagnosis and training system 100. The system includes a computer 102 coupled one or more actuators 104, and one or more sensors 106. When the system is configured for use as a cognitive timing training system, the system 100 may also include one or more feedback devices 110. In some embodiments, feedback is provided to the subject via the actuators 104. The one or more actuators 104 may include a display device for presenting visual stimuli to a subject, audio speakers for presenting audio stimuli, a combination of the aforementioned, or one or more other devices for producing or presenting sequences of stimuli to a subject. The one or more sensors 106, may be mechanical, electrical, electromechanical, auditory (e.g., microphone), visual sensors (e.g., a digital video camera) or other type of sensors (e.g., a frontal brain electroencephalograph, and known as an EEG). The job of the one or more sensors 106 is to detect responses by a subject to sequences of stimuli presented by the one or more actuators 102. Some types of sensors produce large amounts of raw data, only a small portion of which can be considered to be indicative of the user response. In such systems, the sensor or computer 102 contain appropriate filters and/or software procedures for analyzing the raw data so as to extract "sensor signals" indicative of the subject's response to the stimuli. In embodiments in which the one or more sensors 106 includes an electroencephalograph (EEG), the relevant sensor signal from the EEG may be a particular component of the signals produced by the EEG, such as the contingent negative variation (CNV) signal or the readiness potential signal.

The one or more feedback devices 110 can be any device appropriate for providing feedback to the subject. The one or more feedback devices 110 provide real time performance information to the subject corresponding to measurement results, which enables the subject to try to improve his/her anticipatory timing performance. In some embodiments, the performance information provides positive feedback to the subject when the subject's responses (e.g., to sequences of stimuli) are within a normal range of values. In some embodiments, the one or more feedback devices 110 may activate the one or more actuators 104 in response to positive performance from the subject, such as by changing the color of the visual stimuli or changing the pitch or other characteristics of the audio stimuli.

Figure 4:
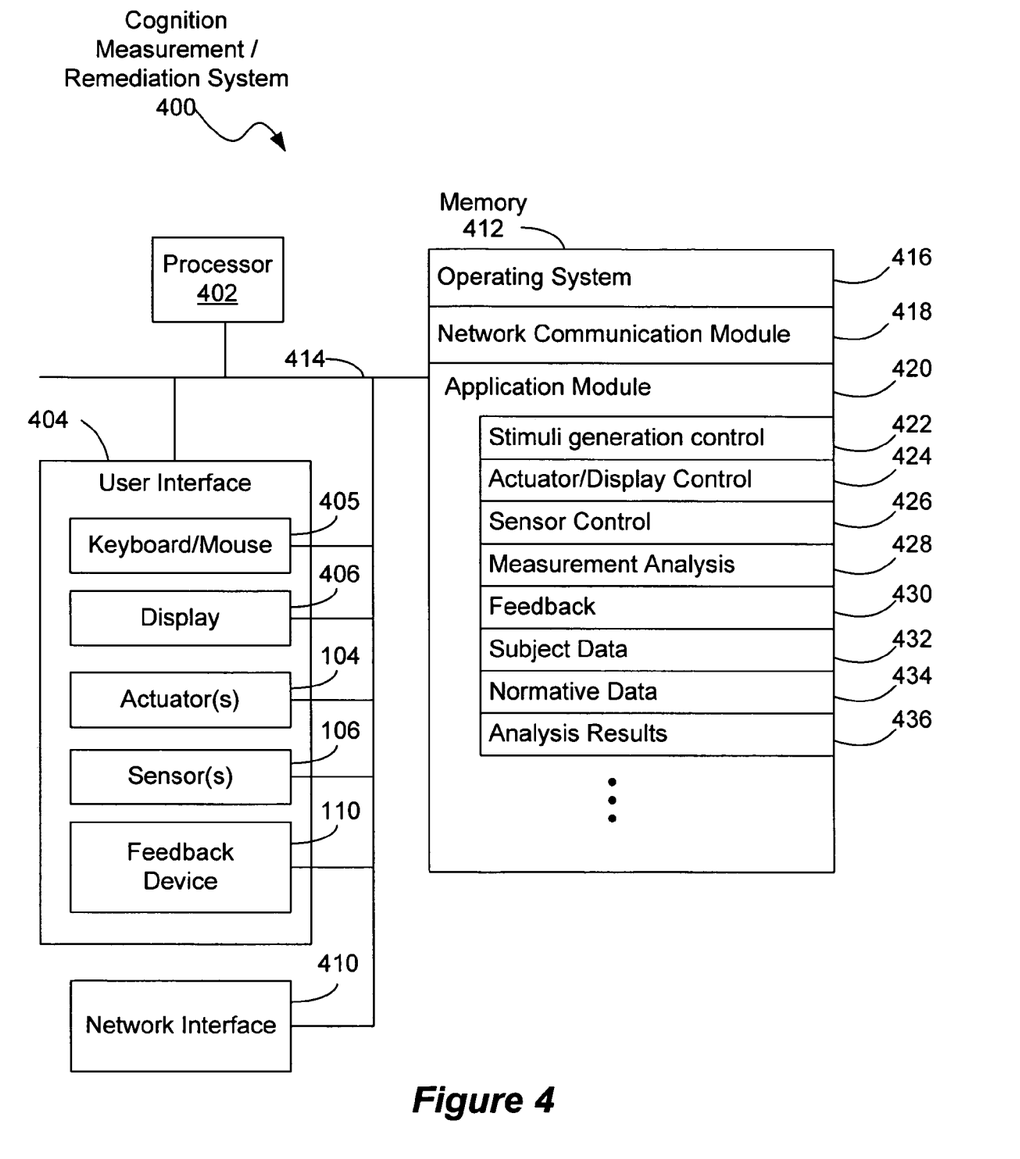
FIG. 4 is a detailed block diagram of a cognition timing diagnosis and training system.

FIG. 4 is a block diagram of a cognition timing diagnosis and training (or remediation) system 400. The system 400 generally includes one or more processors 402, such as CPUs, a user interface 404, memory 412, and one or more communication buses 414 for interconnecting these components. The system 400 may optionally include one or more network or other communications interfaces 410, such as a network interface for conveying testing or training results to another system or device. The user interface 404 includes at least one or more actuators 104 and one or more sensors 106, and may also include one or more feedback devices 110, as discussed above. In some embodiments, the user interface 404 may further include additional computer interface devices such as a keyboard and/or mouse 405 and a display 406 (although the display may one of the actuators 104).

Memory 412 may include high speed random access memory and may also include non-volatile memory, such as one or more magnetic disk storage devices. Memory 412 may include mass storage that is remotely located from the central processing unit(s) 402. The memory 412 stores an operating system 416 (e.g., Microsoft Windows, Linux or Unix), an application module 420, and may optionally store a network communication module 418. The application module 420 may include:

- a stimuli generation control program, module or instructions 422, for generating sequences of stimuli, as described elsewhere in this document;
- an actuator or display control program, module or instructions 424, for producing or presenting the sequences of stimuli to a subject;
- a sensor control program, module or instructions 426, for receiving sensor signals and, where appropriate, analyzing raw data in the sensor signals so as to extract sensor signals indicative of the subject's response to the stimuli; the sensor control program, module or instructions 426 may also include instructions for controlling operation of the one or more sensors 106;
- a measurement analysis program, module or instructions 428, for analyzing the sensor signals to produce measurements and analyses, as discussed elsewhere in this document; and
- a feedback program, module or instructions 430, for generating feedback signals for presentation to the subject via the one or more actuators or feedback devices.

The application module 420 may furthermore store subject data 432, which includes the measurement data for a subject, and optionally may also include analysis results and the like. The application module 420 may also store normative data 434, which includes measurement data from one or more control groups of subjects, and optionally may also include analysis results 436, and the like, based on the measurement data from the one or more control groups.

Still referring to FIG. 4, in an exemplary embodiment, the one or more sensors 106 include a digital video camera focused on the subject's pupil, operating at a picture update rate of at least 200 hertz. In some embodiments the digital video camera is an infrared camera, while in other embodiments the camera may operate in other portions of the electromagnetic spectrum. The resulting video signal is analyzed by the one or more CPU's 402, under the control of the measurement analysis program, module or instructions 428, to determine the screen position(s) where the subject focused, and the timing of when the subject focused at one or more predefined screen positions.

Figure 5:
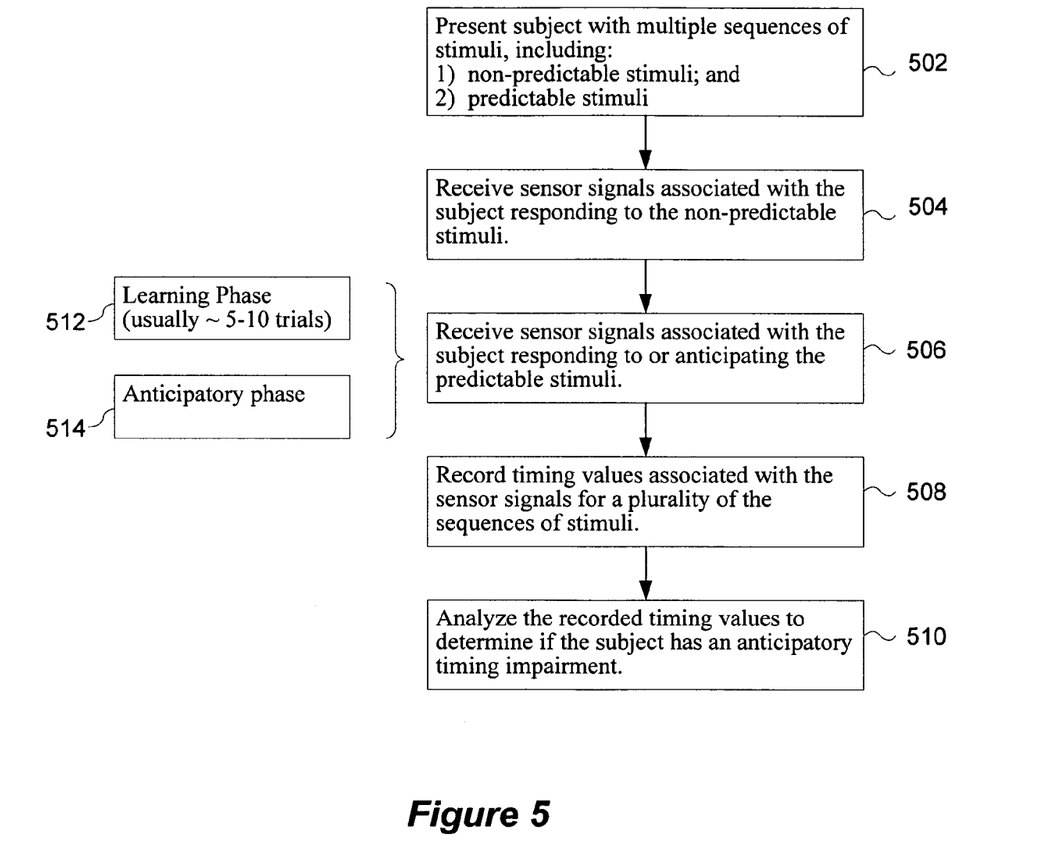
FIG. 5 is a flow chart of a cognition timing diagnosis method.

Referring to FIG. 5, in an embodiment of a method of analyzing a subject's ability to anticipate predictable stimuli, the subject is presented with multiple sequences of stimuli, including sequences of non-predictable stimuli and sequences of predictable stimuli (502). Sensor signals associated with the subject responding to the non-predictable stimuli are received (504). Similarly, sensor signals associated with the subject responding to the predictable stimuli are received (506). In some embodiments, sensor signals associated with the subject responding to the predictable stimuli are received during an initial learning phase (512) followed by an anticipatory phase (514), as described above in relation to FIG. 2a. In some embodiments, the learning phase lasts five to ten sequences of stimuli (trials). Timing values associated with the sensor signals are recorded for a plurality of sequences of stimuli (508). The recorded timing information is analyzed to determine if the subject has an anticipatory timing impairment (510). In some embodiments, a report is generated to present the analysis.

Figure 6:
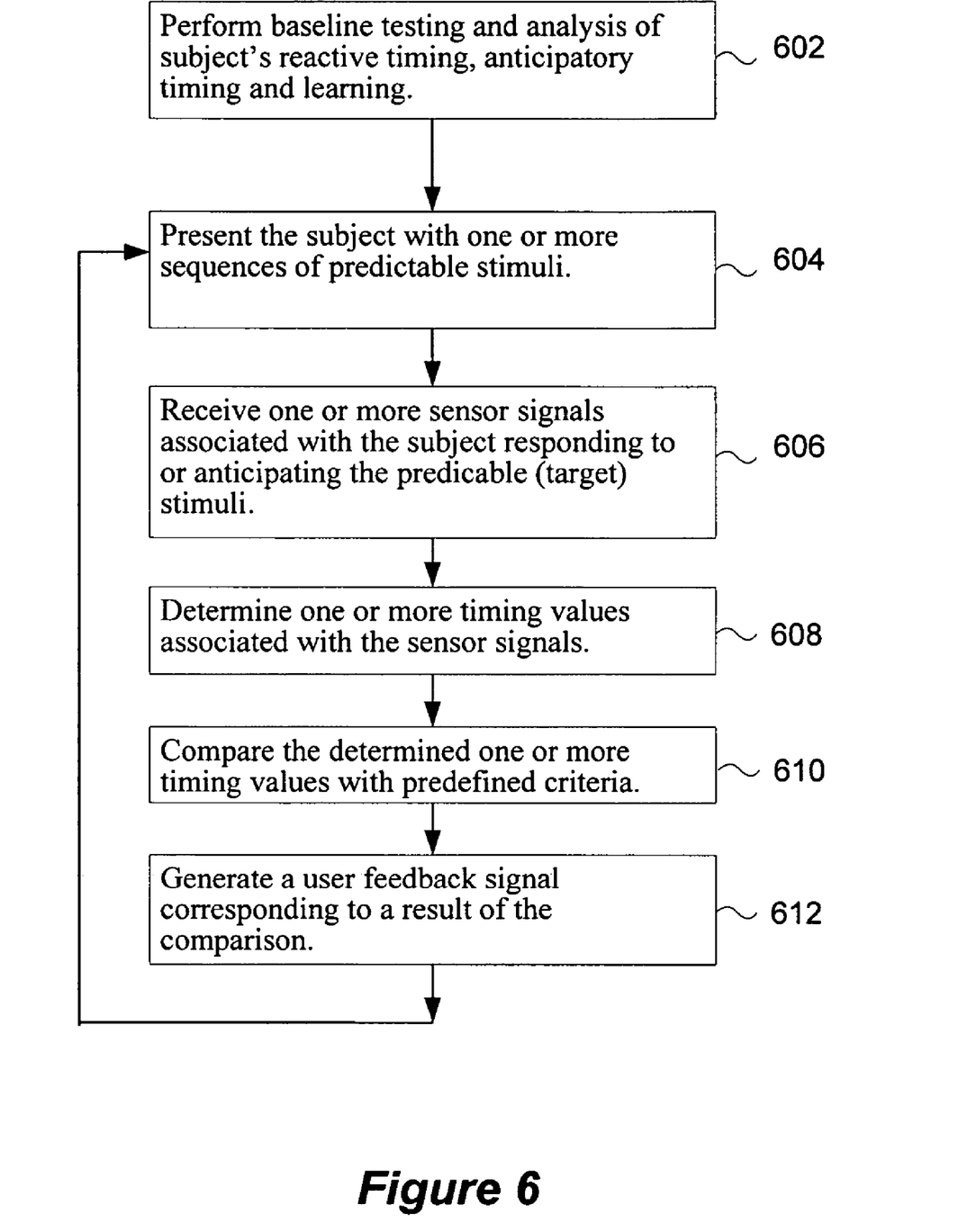
FIG. 6 is a flow chart of an anticipatory timing remedial training method.

Referring to FIG. 6, in an embodiment of a method of training a subject to improve his/her response times to predictable stimuli, the baseline testing and analysis is performed to determine and/or analyze a subject's reactive timing, anticipatory timing and learning (602). This may correspond to a method similar to the one represented by the flow chart in FIG. 5.

Next, a sequence of training steps 604-612 are repeatedly performed so as to help train a subject to improve his/her anticipatory timing. Such training exercises portions of the subject's brain that are responsible for cognitive tasks associated with anticipating events. By focusing the training narrowly on those cognitive tasks associated with anticipating events, appropriate portions of the brain are stimulated, which causes the brain to find ways to improve the subject's ability to anticipate the timing of predictable events.

In some embodiments, the training steps include presenting the person with one or more sequences of predictable stimuli (604) and receiving sensor signals associated with the subject responding to or anticipating the predictable stimuli (606). The sequences of predictable stimuli may include precursor stimuli and target stimuli, with the precursor stimuli providing the subject the information needed to predict the target stimuli. For example, the precursor stimuli may display an arrow pointing to the area in which a visual stimulus will shortly appear. Timing values associated with the sensor signals are determined (608) and compared with predefined criteria, such as baseline data for one or more control subjects (610). Based on the results of the comparison, a subject feedback signal corresponding to the results may be generated (612). In some embodiments, only positive feedback signals are generated, to reward performance meeting predefined or individually determined performance goals. In other embodiments, the feedback signals include negative feedback signals that indicate failure to meet the performance goals. In still other embodiments the feedback signals may include gradations to indicate the extent to which the subject has met or failed to meet the performance goals.

Diagnosis and Training Using Measurements of Smooth Pursuit

Figure 7:
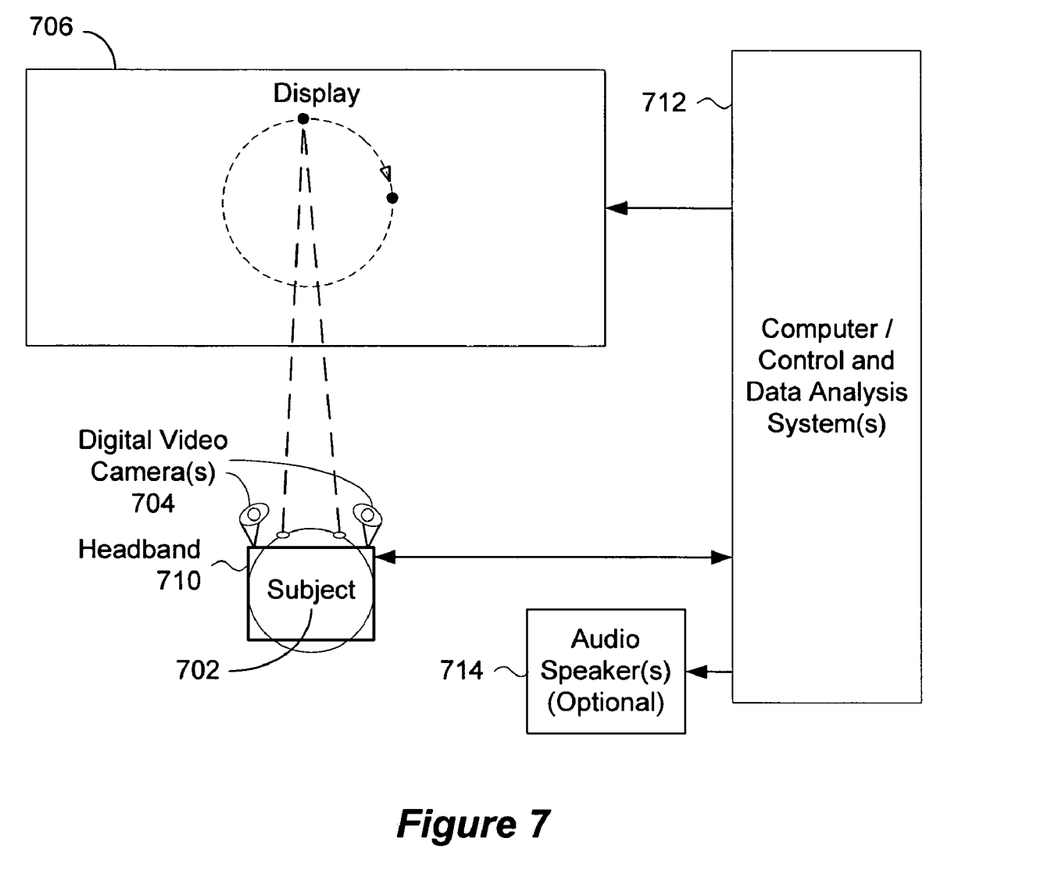
FIG. 7 depicts a system for measuring a subject's ability to visually track a smoothly moving object, repeatedly moving over a tracking path.

Referring to FIG. 7, in some embodiments a subject 702 is shown a smoothly moving image 704, such as a dot or ball following a circular or oval path (sometimes called the tracking circle or tracking path) on a screen 706. A digital video camera 708, or a pair of such cameras, is focused on one or both eyes of the subject so that eye movement of the subject are recorded. In some embodiments, the digital video cameras are mounted on the subject's head by a headband 710. Various mechanisms may be used to stabilize the subject's head, for instance to keep the distance between the user and the screen 706 fixed, and to also keep the orientation of the user's head fixed as well. The screen 706 may be a television screen, computer monitor or other display device. The screen 706 and the digital video camera(s) 708 are coupled to a computer or control system 712. The control system 712 controls the patterns displayed and also receives and analyses the eye position information received from the digital video camera(s) 708.

In one embodiment, the distance between the user 702 and the screen 706 is kept fixed at approximately 40 cm; in other embodiments the distance between the user 702 and the screen 706 is kept fixed at a distance in the range of 30 to 100 cm. More generally, the distance between the user and the screen is determined by the size of the tracking circle or path, as measured in terms of the range of horizontal angles and vertical angles between the user's eye and the tracking circle of the moving object. The range of horizontal angles and vertical angles between the user's eye and the tracking circle is typically between 3 and 10 degrees (i.e., the difference between the maximum and minimum angles—vertical or horizontal—ranges between 3 and 10 degrees). Furthermore, the size of the tracking circle and the distance between the subject 702 and the screen 706 are selected so that the average angular velocity of the subject's eyes while following the moving image over the tracking circle is less than a predefined maximum average eye velocity. The predefined maximum average eye velocity during each smooth pursuit test is typically less than 25 degrees per second, and more generally is less than 50 degrees per second.

In order to provide accurate and meaningful real time measurements of where the user's is looking at any one point in time, the eye position measurements produced by the digital video cameras 708 may be calibrated by having the subject focus on a number of points on the screen 706 during a calibration phase or process. For instance, calibration may be based on nine points displayed on the screen, including a center point, positioned at the center of the screen locations to be used during testing of the subject, and eight points along the periphery of the screen region to be used during testing of the subject. For instance, the eight points may correspond to locations having angular positions at 45 degree increments with respect to a center point. The subject is asked to focus on each of the calibration points, in sequence, while the digital video cameras 708 measure the pupil or eye position of the subject. The resulting measurements are then used by the computer or control system 712 to produce a mapping of eye position to screen location, so that the system can determine the position of the screen at which the user is looking at any point in time. In other embodiments, the number of points used for calibration may be more or less than nine points (e.g., the number of calibration points may range from 5 to 17 points), and the positions of the calibration points may distributed on the screen in various ways.

The calibration process may be performed each time a subject is to be tested, because small differences in head position relative to the cameras, and small differences in position relative to the screen 706, can have a large impact on the measurements of eye position, which in turn can have a large impact on the determination of the screen position at which the subject is looking. The calibration process can also be used to verify that the subject 702 has a sufficient range of oculomotor movement to perform the test.

After calibration is completed, the subject is told to focus on (i.e., visually follow) the object (e.g., a dot or ball) on the screen and to do their best to remain focused on the ball as it moves. The displayed object is then smoothly and repeatedly moved over a tracking path, such as a circular or oval path. In some embodiments, the rate of movement of the displayed object is constant for multiple orbits around the tracking path. The rate of movement of the displayed object, measured in terms of revolutions per second (i.e., Hertz), may be as low as 0.1 Hz and as high as 3 Hz. However, it has been found that the most useful measurements are obtained when the rate of movement of the displayed object is in the range of about 0.4 Hz to 1.0 Hz, and more generally when the rate of movement of the displayed object is in the range of about 0.2 Hz to 2.0 Hz. A rate of 0.4 Hz corresponds to 2.5 seconds for the displayed object to traverse the tracking path, while a rate of 1.0 Hz corresponds to 1.0 seconds for the displayed object to traverse the tracking path. Even healthy subjects have been found to have trouble following a displayed object that traverses a tracking path at a repetition rate of more than about 2.0 Hz.

In one embodiment, the subject is asked to following the moving object for two sets of twenty clockwise circular orbits, with a rest period between. The angular amplitude of the moving object, as measured from the subject's eyes, is about 5 degrees in the horizontal and vertical directions. In other embodiments, the angular amplitude of the moving object is in the range of 3 to 10 degrees. The circular eye movement of the subject, while following the moving displayed object, can be divided into horizontal and vertical components for analysis. Thus, as many as four sets of measurements may be made of the subject's eye movements while performing smooth pursuit of a moving object: left eye horizontal position, left eye vertical position, right eye horizontal position, and right eye vertical position. Ideally, if the subject perfectly tracked the moving object at all times, each of the four positions would vary sinusoidally over time. That is, a plot of each component (horizontal and vertical) of each eye's position over time would follow the function $\sin(\omega t+\theta)$, where $\sin(\ )$ is the sine function, $\theta$ is an initial angular position, and co is the angular velocity of the subject's eye. Alternately, one or two sets of two dimensional measurements (based on the movement of one or two eyes of the subject) may be used for analysis of the subject's ability to visually track a smoothly moving displayed object.

In some embodiments, the video cameras 704 take pictures of the subject's eye or eyes at least 400 times per second (i.e., the video cameras having a picture frame rate of at least 400 frames per second). For instance, in some embodiments, the video cameras 704 take pictures of the subject's eye or eyes about 500 times per second, or about once every 2 milliseconds. Thus, during each orbit of the displayed object, the video cameras 704 take between 200 and 1250 pictures of each eye, thereby providing a significant amount of data on which to base statistical analysis of the subject's ability to visually follow a smooth pursuit moving object. The video cameras 704 take thousands of pictures during each block of twenty revolutions of the displayed object, and thereby provide thousands of measurements of the subject's performance.

Smooth pursuit eye movement is an optimal movement to assess anticipatory timing in intentional attention (interaction) because it requires attention. Furthermore, as discussed in more detail below, measurements of a subject's point of focus while attempting to smoothly pursue a moving displayed object can be analyzed so as to provide one or more metrics, such as a metric of attention, a metric of accuracy, a metric of variability, and so on.

For each block of N orbits or revolutions of the displayed object, the pictures taken by the cameras are converted into screen locations (hereinafter called subject eye positions), indicating where the subject was looking at each instant in time recorded by the cameras, and then the subject eye positions are compared with the actual displayed object positions. The data representing eye and target movements may be low-pass filtered (e.g., at 50 Hz) to reduce signal noise. Saccades, which are fast eye movements during which the subject catches up with the moving displayed object, may be detected and counted. In some embodiments, eye position measurements during saccades are replaced with extrapolated values, computed from eye positions preceding each saccade. In some other embodiments, eye position and velocity data for periods in which saccades are detected are removed from the analysis of the eye position and velocity data. The resulting data is then analyzed to generate one or more of the following derived measurements or statistics:

Visual feedback delay, which is the latency between the response (eye velocity) and the stimulus (target velocity), which may be obtained by conducting a linear regression fit, using equation 1, below, between the response and the stimulus with different values of $\tau$ and then identifying the "best fit" value of $\tau$, herein called the visual feedback delay.

$$\text{Eye } Vel(t) = \text{Target } Vel(t+\tau) \qquad \text{(Equation 1)}$$

where "t" is time, "Eye (t)" is eye velocity (measured in units, for example, of degrees per second) measured as a function of time, "Target (t+$\tau$)" is a target velocity as a function of time, and $\tau$ is the visual feedback delay. The best fit value of $\tau$ may be determined, for example, by using a least squares technique to identify the value of $\tau$ that produces the smallest error magnitude, where the error is computed as $$\sum_t ((\text{Eye } Vel(t) - \text{Target } Vel(t+\tau))^2.$$

Frequency of Saccades, which is the average number of times eye velocity exceeds a predefined threshold velocity (e.g., 100 degrees per second) per cycle or revolution of the displayed target. Alternately, instead of computing a frequency of saccades, the system or method may determine the number of saccades over a predefined number of revolutions (e.g., five revolutions, or twenty revolutions) of the displayed target.

Position error (accuracy index), is defined by:

$$Epos = |\text{Eye } Pos(t) - \text{Target } Pos(t)| \qquad \text{(Equation 2)}$$

where "t" is time, and "Epos" is the distance between eye position (Eye Pos (t)) and target position (Target Pos (t)); eye position, target position and Epos may all be measured in units of degrees; Epos may be averaged over multiple cycles or revolutions of the displayed target to produce an average position error, herein called the subject's accuracy index.

Intra-Individual Variability of Position Error, may be defined as the standard deviation of Epos, the position error, for a particular individual. The variability of position error is sometimes called the subject's attention index.

Gain, is the ratio between eye and target velocity:

$$Egain = |\text{Eye } Vel(t) / \text{Target } Vel(t)| \qquad \text{(Equation 3)}$$

where Egain is the gain, "t" is time, and "Eye Vel (t)" is eye velocity, and "Target Vel (t)" is target velocity; Egain is sometimes larger than 1 and sometimes smaller than 1. Gain (i.e., Egain) may be evaluated at all or a subset of the times at which eye position is measured. Gain may be averaged over multiple cycles or revolutions of the displayed target:

Intra-Individual Variability of Gain, may be defined as the standard deviation of Egain for a particular individual. In other embodiments, other techniques may be used to derive an Intra-Individual Variability of Gain from a subject's Egain values.

One or more of the above identified derived measurements are obtained for a subject, and then compared with the derived measurements for other individuals or with the derived measurements for the same subject at an earlier time. Changes in one or more derived measurements for a particular person can be used to evaluate improvements or deterioration in the person's ability to anticipate events.

The derived measurements that relate to variability of a person's tracking a smooth pursuit target, such as variability of position error and variability of eye velocity gain, are metrics of the person's attention, which corresponds to a person's ability to concentrate on a task and to anticipate predictable, future events. An index of attention (or more generally an attention metric) may be defined as the intra-individual variability of eye position, the intra-individual variability of eye velocity gain, or a combination of these. Alternately, the attention metric or index may be defined as a metric selected from the set consisting of consisting of (A) an intra-individual variability of gain metric, (B) an intra-individual variability of position error metric, (C) an average position error metric, (D) a visual feedback delay metric, (E) a number or frequency of saccades metric and (F) a mathematical combination (e.g., a linear, weighted combination) of two or more of the aforementioned metrics.

The optimal timeframe for each cycle or revolution of a smooth pursuit moving target, for purposes of measuring a person's ability to visually follow a smooth pursuit moving target, is related to the length of time that is experienced by the person as a single moment in time. A moment in time is experienced by most persons as a period having duration between 0.5 and 3 seconds. During measurements on a number of subjects, the lowest position error variability and best anticipation were measured when the rate of movement of the displayed object, measured in terms of revolutions per second (i.e., Hertz), is between 0.4 Hz and 1.0 Hz (i.e., the moving target completes each orbit of its tracking path in a time period that ranges from 2.5 seconds to 1.0 seconds). Smooth pursuit target movement rates above or below this rate produce more variability and less anticipation. There is also evidence that if a subject concentrates on a difficult cognitive task, the present moment as experienced by the subject stretches out to a longer period of time, for example from 1 second to 2.5 seconds. The mechanism for this is the additional time needed to anticipate sensory information in more complex tasks.

Attention can be distracted and fatigued. Both of these functions can be measured with smooth pursuit eye movements. Decreased attention, caused by fatigue or a distractor, can be measured by monitoring error and variability during smooth eye pursuit. As the subject decreases attention there is an increase in position error variability and decreased anticipation. An example of a distractor is an auditory distractor task such as counting high tones in a mixture of high and low tones presented to the subject through headphones. Another example of a distractor is a mental task, such as a memory task (e.g., recalling information presented to the subject immediately prior to the smooth eye pursuit monitoring test). Other distractors that require attention can be used. The more difficult the distractor, the more attention is taken away from smooth eye pursuit, which results in increased variability in eye position. In some embodiments, an index of distractibility (or more generally, a distractibility metric) is defined as the difference in a predefined or selected measurement or metric between a first smooth pursuit test, or a portion thereof, during which the subject is not subjected to a distractor, and a second smooth pursuit test, or a portion thereof, during which the subject is exposed to a distractor. Alternately, the index of distractibility is defined as the ratio of the predefined or selected measurement or metric between the two smooth pursuit tests (i.e., one without a distractor and one with a distractor). The predefined or selected measurement or metric that forms the basis of the index of distractibility may be selected from the group consisting of (A) intra-individual variability of gain, (B) intra-individual variability of position error, (C) average position error, (D) visual feedback delay, (E) number or frequency of saccades, and (F) a mathematical combination of two or more of the aforementioned measurements or metrics.

A subject's susceptibility to fatigue can be measured by the subject's ability, or inability, to maintain low variability and anticipation over the course of a smooth pursuit test. Subjects whose performance during a smooth pursuit test quickly degrades over a short period of time (e.g., less than 10 or 20 orbits of the displayed target over the tracking path) cycles have a high potential for fatigue. In some embodiments, an index of fatigue (or more generally, a fatigue metric) is defined as the change in a predefined or selected measurement or metric between a first portion of a smooth pursuit test (e.g., during the first five orbits of the moving target) and a second portion of the smooth pursuit test (e.g., the third or fourth set of five orbits of the moving target). Alternately, the index of fatigue is defined as the ratio of the predefined or selected measurement or metric between two portions (e.g., a late portion and an early portion) of a smooth pursuit test. The predefined or selected measurement or metric that forms the basis of the index of distractibility may be selected from the group consisting of (A) intra-individual variability of gain, (B) intra-individual variability of position error, (C) average position error, (D) visual feedback delay, (E) number or frequency of saccades and (F) a mathematical combination of two or more of the aforementioned measurements or metrics. Thus, the definitions of the index of distractibility and the index of fatigue may be similar or even identical. However, in some embodiments, the index of distractibility corresponds to a degradation of performance when a subject is exposed to a distractor, while the index of fatigue corresponds to subject's degradation of performance over time without exposing the subject to a distractor.

Smooth pursuit of a target moving over a circular path can also be used for rehabilitative training, using the methodology described above with respect to FIG. 6. An important aspect of cognition and attention is timing. When a person's timing in performing everyday tasks is sub-standard, there is a decline in the quality of the person's performance of those tasks. Use of feedback techniques in conjunction with smooth pursuit can reduce variability of position and variability of gain, which improves the subject's ability to maintain attention and to anticipate events. While a subject is engaging in a smooth pursuit test, or between sets of smooth pursuit cycles, the subject is given feedback on eye position and variability. The feedback can be aural, with suggestions on how to perform better. The feedback can be visual, with a display on screen showing where the subject was actually focused during a prior test, compared with the position of the moving target, and perhaps showing instances in which the subject variability increased. Training the subject to reduce variability leads to anticipatory eye movements with less variability. This will then generalize to cognitive functions, since the common substrate of smooth pursuit and attention is timing.

Thus, the less the variability in eye movement the better attention becomes, so that improving (i.e., reducing) variability will generalize to improved performance in cognitive and motor tasks requiring attention. Essentially the key component of attention is the process of reducing variability. If anticipatory timing is impaired (due to fatigue, aging or clinical conditions) then variability will increase and the subject will have impaired attention—as evidenced by increased distractibility and poor performance. Remedial training to give feedback on anticipatory timing allows the subject to improve timing and thereby reduce variability. The reduction in variability allows the subject to concentrate (attend) and become less distractible. This improved temporal processing will then generalize in improved motor and cognitive performance during tasks that require attention. Also, since attention is essential for learning and memory, these functions will also improve. As a consequence remedial learning in anticipatory timing actually accelerates as attention improves.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method of testing a subject for cognitive impairment, comprising:
   presenting the subject with a display of a smoothly moving object, repeatedly moving over a tracking path;
   measuring the subject's eye movements during the presenting;
   comparing the measured eye movements with movements of the smoothly moving object to generate an error signal, the error signal corresponding to at least one of timing error, position error and velocity error of the subject's eye movements during visual pursuit of the display of the smoothly moving object;
   analyzing variability of the error signal during visual pursuit of the display of the smoothly moving object to generate a variability metric, wherein the variability metric corresponds to how accurately and how consistently the subject visually tracks movement of the object; and
   presenting a report, based on at least the variability metric, that indicates whether the subject has a cognitive impairment.

2. The method of claim 1, wherein the cognitive impairment is an anticipatory timing impairment.

3. The method of claim 1, wherein the tracking path of the moving object is a circular path.

4. The method of claim 1, wherein the smoothly moving object is displayed so as to repeat its movement over the tracking path with a frequency between 0.2 and 2.0 Hz.

5. The method of claim 1, wherein the variability metric is selected from the set consisting of a variability of eye position error metric, a variability of eye velocity gain metric, an eye position error metric, a rate or number of saccades metric, a visual feedback delay metric, and a combination of two or more of said metrics.

6. The method of claim 1, wherein the analyzing includes generating a metric selected from the set consisting of a metric of fatigability and a metric of distractibility.

7. The method of claim 1, wherein measuring the subject's eye movements is accomplished using one or more video cameras having a picture frame rate of at least 400 frames per second.

8. The method of claim 1, wherein the analyzing includes generating an index of distractibility, indicative of the subject's susceptibility to distraction.

9. The method of claim 8, including presenting auditory distraction to the subject while presenting the subject with the display of the smoothly moving object.

10. The method of claim 1, wherein the analyzing compares values determined for the subject with predetermined criteria associated with subjects having normal anticipatory timing.

11. A method of training a subject to improve anticipatory timing, comprising:
   presenting the subject with stimuli comprising a display of a smoothly moving object, repeatedly moving over a tracking path;
   measuring the subject's eye movements during the presenting;
   comparing the measured eye movements with movements of the smoothly moving object to generate an error signal, the error signal corresponding to at least one of timing error, position error and velocity error of the subject's eye movements during visual pursuit of the display of the smoothly moving object;
   analyzing variability of the error signal during visual pursuit of the display of the smoothly moving object to generate a variability metric, wherein the variability metric corresponds to how accurately and how consistently the subject visually tracks movement of the object; and
   presenting a subject feedback signal based on at least the variability metric.

12. The method of claim 11, including repeating the presenting, determining, comparing and generating operations multiple times so as to generate a sequence of subject feedback signals, thereby enabling the subject to adjust their response to the stimuli in accordance with the subject feedback signals.

13. A system for testing a subject for cognitive impairment, comprising:
   a display to present to the subject stimuli comprising a smoothly moving object, repeatedly moving over a tracking path;
   a video sensor for measuring eye movements of the subject; and
   a computer configured to:
      present, on the display, the smoothly moving object, repeatedly moving over the tracking path;
      measure, using the video sensor, the subject's eye movements during the presenting;
      compare the measured eye movements with movements of the smoothly moving object to generate an error signal, the error signal corresponding to at least one of timing error, position error and velocity error of the subject's eye movements during visual pursuit of the display of the smoothly moving object;
      analyze variability of the error signal during visual pursuit of the display of the smoothly moving object to generate a variability metric, wherein the variability metric corresponds to how accurately and how consistently the subject visually tracks movement of the object; and
      present a report, based on at least the variability metric, that indicates whether the subject has a cognitive impairment.

14. The system of claim 13, wherein the cognitive impairment is an anticipatory timing impairment.

15. The system of claim 13, wherein the tracking path of the moving object is a circular path.

16. The system of claim 13, wherein the smoothly moving object is displayed so as to repeat its movement over the tracking path with a frequency between 0.2 and 2.0 Hz.

17. The system of claim 13, wherein the variability metric is selected from the set consisting of a variability of eye position error metric, a variability of eye velocity gain metric, an eye position error metric, a rate or number of saccades metric, a visual feedback delay metric, and a combination of two or more of said metrics.

18. The system of claim 13, wherein the video sensor comprises one or more video cameras having a picture frame rate of at least 400 frames per second.

* * * * *